(12) United States Patent
Ahlheim et al.

(10) Patent No.: US 7,759,308 B2
(45) Date of Patent: Jul. 20, 2010

(54) MICROPARTICLES COMPRISING SOMATOSTATIN ANALOGUES

(75) Inventors: Markus Ahlheim, Staufen (DE); Michael Ausborn, Lörrach (DE); Olivier Lambert, Spechbach-le-Haut (FR); Marc Riemenschnitter, Freiburg (DE)

(73) Assignee: Novartis AG, Basel (CH)

( * ) Notice: Subject to any disclaimer, the term of this patent is extended or adjusted under 35 U.S.C. 154(b) by 712 days.

(21) Appl. No.: 10/579,186

(22) PCT Filed: Nov. 12, 2004

(86) PCT No.: PCT/EP2004/012870

§ 371 (c)(1),
(2), (4) Date: Dec. 19, 2006

(87) PCT Pub. No.: WO2005/046645

PCT Pub. Date: May 26, 2005

(65) Prior Publication Data

US 2007/0212418 A1    Sep. 13, 2007

(30) Foreign Application Priority Data

Nov. 14, 2003  (GB) ................. 0326602.0
Mar. 19, 2004  (GB) ................. 0406241.0

(51) Int. Cl.
*A61K 38/12* (2006.01)

(52) U.S. Cl. .................. 514/11; 530/317; 977/788

(58) Field of Classification Search ....................... None
See application file for complete search history.

(56) References Cited

U.S. PATENT DOCUMENTS 5,639,480 A     6/1997  Bodmer et al.
5,876,761 A *   3/1999  Bodmer et al. .............. 424/501

FOREIGN PATENT DOCUMENTS

| EP | 1 240 896 | 9/2002 |
|----|-----------|--------|
| GB | 2234896 | 2/1991 |
| WO | 97/01579 | 1/1997 |
| WO | 98/32423 | 7/1998 |
| WO | 01/12233 | 2/2001 |

OTHER PUBLICATIONS

Lamberts, 2002, European Journal of Endocrinology, 146, 701-705.*
Bruns, 2002, The Expanding Role of Octreotide II: Advances in Endocrinology and Eye Diseases, Eds SWJ Lamberts & E. Ghico, pp. 251-254.*
Bodmer, Journal of Controlled Release, 1992, 21, 129-138.*
Pistel, Journal of Controlled Release, 1999, 59, 309-325.*

* cited by examiner

*Primary Examiner*—Andrew D Kosar
*Assistant Examiner*—Satyanarayana R Gudibande
(74) *Attorney, Agent, or Firm*—Jennifer Chapman; Lydia T. McNally

(57) ABSTRACT

Disclosed are microparticles comprising a somatostatin analogue embedded in a biocompatible pharmacologically acceptable polymer matrix for a long acting release and pharmaceutical compositions comprising such microparticles.

11 Claims, No Drawings

MICROPARTICLES COMPRISING SOMATOSTATIN ANALOGUES

BACKGROUND OF THE INVENTION

The present invention relates to microparticles comprising a somatostatin analogue and to pharmaceutical compositions comprising the same.

SUMMARY OF THE INVENTION

Somatostatin is a tetradecapeptide having the structure

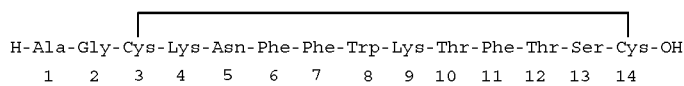

Somatostatin analogues of particular interest have been described e.g. in WO 97/01579 and WO 02/10192. Said somatostatin analogues comprise the amino acid sequence of formula I

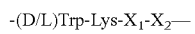

wherein $X_1$ is a radical of formula (a) or (b)

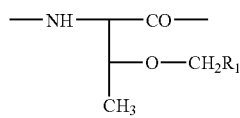

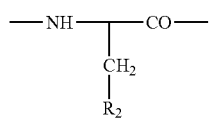

$R_2$ is $-Z_1-CH_2-R_1$, $-CH_2-CO-O-CH_2-R_1$,

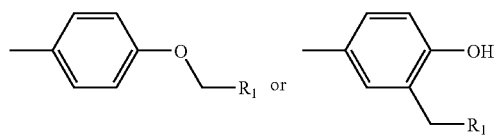

wherein $R_1$ is a phenyl optionally substituted by halogen, methyl, ethyl methoxy or ethoxy.

$Z_1$ is O or S, and $X_2$ is an α-amino acid having an aromatic residue on the $C_\alpha$ side chain, or an amino acid unit selected from Dab, Dpr, Dpm, His, (Bzl)HyPro, thienyl-Ala, cyclohexyl-Ala and t-butyl-Ala, the residue Lys of said sequence corresponding to the residue $Lys^9$ of the native somatostatin-14.

These compounds are referred to hereinafter as compounds of the invention.

By somatostatin analogue as used herein is meant a straight-chain or cyclic peptide derived from that of the naturally occurring somatostatin-14, comprising the sequence of formula I and wherein additionally one or more amino acid units have been omitted and/or replaced by one or more other amino acid radical(s) and/or wherein one or more functional groups have been replaced by one or more other functional groups and/or one or more groups have been replaced by one or several other isosteric groups. In general the term covers all modified derivatives of the native somatostatin-14 comprising the above sequence of formula I which have binding affinity in the nM range to at least one somatostatin receptor subtype as defined hereinafter.

Preferably, the somatostatin analogue is a compound in which the residues at positions 8 through 11 of the somatostatin-14 are represented by the sequence of formula I as defined above.

More preferably, the somatostatin analogue is a compound as disclosed above comprising a hexapeptide unit, the residues at positions 3 through 6 of said hexapeptide unit comprising the sequence of formula I. Particularly preferred is a somatostatin hexapeptide wherein the residues at positions 1 and 2 of the hexapeptide unit may be any of those as known in the art, e.g. as disclosed by A. S. Dutta in Small Peptides, Vol. 19, 292-354, Elsevier, 1993, or as substituents for, $Phe^6$ and/or $Phe^7$ of somatostatin-14.

More particularly the somatostatin analogue is a compound in which the hexapeptide unit is cyclic, e.g. having a direct peptide linkage between the α-carbonyl group of the residue at position 6 and the α-amino group of the residue at position 1.

While Lys, $X_1$ and $X_2$ in the sequence of formula I have the L-configuration, Trp may have the D- or L-configuration. Preferably Trp has the D-configuration.

$X_1$ is preferably a residue of formula (a) or (b), $R_2$ being preferably

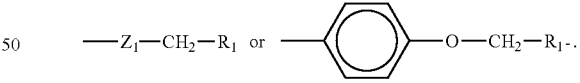

When $X_2$ comprises an aromatic residue on the $C_\alpha$ side chain, it may suitably be a natural or unnatural α-amino acid, e.g. Phe, Tyr, Trp, Nal, Pal, benzothienyl-Ala, Tic and thyronin, preferably Phe or Nal, more preferably Phe. $X_2$ is preferably an α-amino acid bearing an aromatic residue on the $C_u$ side chain.

When $R_1$ is a substituted phenyl, it may suitably be substituted by halogen, methyl, ethyl, methoxy or ethoxy e.g. in ortho and/or para. More preferably $R_1$ is unsubstituted phenyl.

$Z_1$ is preferably O.

Representative compounds of the invention are e.g. compounds of formula (II)

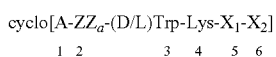
(II)

wherein $X_1$ and $X_2$ are as defined above,

A is a divalent residue selected from Pro,

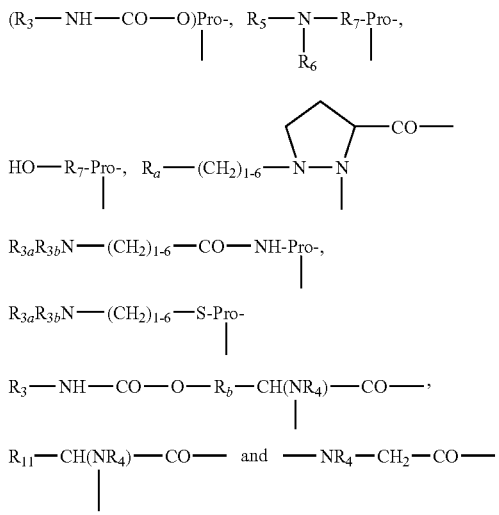

wherein $R_3$ is $NR_8R_9$—$C_{2-6}$alkylene, guanidino-$C_{2-6}$alkylene or $C_{2-6}$alkylene-COON, $R_{3a}$ is H, $C_{1-4}$alkyl or has independently one of the significances given for $R_3$, $R_{3b}$ is H or $C_{1-4}$alkyl, $R_a$ is OH or $NR_5R_6$, $R_b$ is —$(CH_2)_{1-3}$— or —CH($CH_3$)—, $R_4$ is H or $CH_3$, $R_{4a}$ is optionally ring-substituted benzyl, each of $R_5$ and $R_6$ independently is H, $C_{1-4}$alkyl, ω-amino-$C_{1-4}$alkylene, ω-hydroxy-$C_{1-4}$alkylene or acyl, $R_7$ is a direct bond or $C_{1-6}$alkylene, each of $R_8$ and $R_9$ independently is H, ω-hydroxy-$C_{2-4}$alkylene, acyl or $CH_2OH$—$(CHOH)_c$—$CH_2$— wherein c is 0, 1, 2, 3 or 4, or $R_8$ and $R_9$ form together with the nitrogen atom to which they are attached a heterocyclic group which may comprise a further heteroatom, and $R_{11}$ is optionally ring-substituted benzyl, —$(CH_2)_{1-3}$—OH, $CH_3$—CH(OH)— or —$(CH_2)_{1-5}$—$NR_8R_6$, and $ZZ_a$ is a natural or unnatural α-amino acid unit.

$ZZ_a$ may have the D- or L-configuration. When $ZZ_a$ is a natural or unnatural α-amino acid unit, it may suitably be e.g. Thr, Ser, Ala, Val, Ile, Leu, Nle, His, Arg, Lys, Nal, Pal, Tyr, Trp, optionally ring-substituted Phe or $N^α$-benzyl-Gly. When $ZZ_a$ is Phe, the benzene ring thereof may be substituted by e.g. $NH_2$, $NO_2$, $CH_3$, $OCH_3$ or halogen, preferably in para position. When $ZZ_a$ is Phe, the benzene ring thereof is preferably unsubstituted.

When A comprises a Pro amino acid residue, any substituent present on the proline ring, e.g. $R_3$—NH—CO—O— etc., is preferably in position 4. Such substituted proline residue may exist in the cis form, e.g.

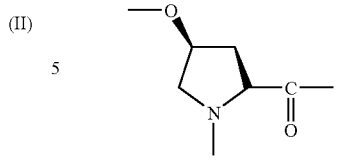

as well as in the trans form. Each geometric isomer individually as well as mixtures thereof are compounds of the invention.

When A is

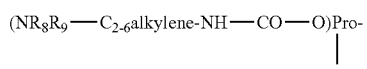

where $NR_8R_9$ forms a heterocyclic group, such group may be aromatic or saturated and may comprise one nitrogen or one nitrogen and a second heteroatom selected from nitrogen and oxygen. Preferably the heterocyclic group is e.g. pyridyl or morpholino. $C_{2-6}$Alkylene in this residue is preferably —$CH_2$—$CH_2$—.

Any acyl as $R_5$, $R_6$, $R_8$ and $R_9$ in A may be e.g. $R_{12}CO$— wherein $R_{12}$ is H, $C_{1-4}$alkyl, $C_{2-4}$alkenyl, $C_{3-6}$cycloalkyl or benzyl, preferably methyl or ethyl. When $R_{4a}$ or $R_{11}$ in A is ring-substituted benzyl, the benzene ring may be substituted as indicated above for $ZZ_a$.

Particularly preferred are compounds of formula III

III

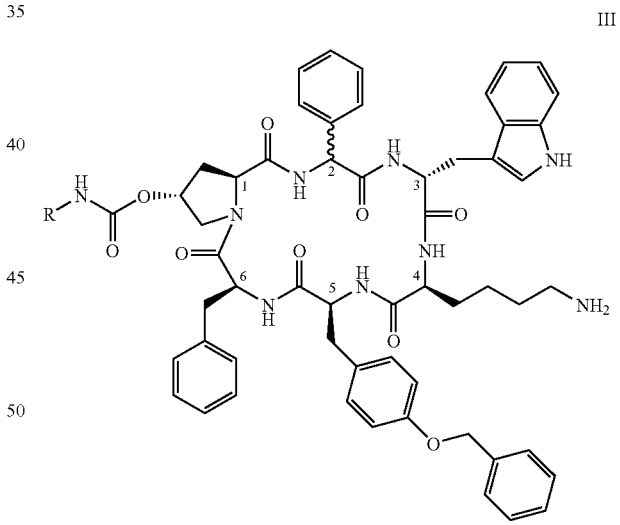

wherein the configuration at C-2 is (R) or (S) or a mixture thereof, and wherein R is $NR_{10}R_{11}$—$C_{2-6}$alkylene or guanidine-$C_{2-6}$alkylene, and each of $R_{10}$ and $R_{11}$ independently is H or $C_{1-4}$alkyl, in free form, in salt form or protected form.

Preferably R is $NR_{10}R_{11}$—$C_{2-6}$alkylene. Preferred compounds of formula III are those wherein R is 2-amino-ethyl, namely cyclo[{4-($NH_2$—$C_2H_4$—NH—CO—O—)Pro}-Phg-DTrp-Lys-Tyr(4-Bzl)-Phe] (referred herein to as Compound A) and cyclo[{4-($NH_2$—$C_2H_4$—NH—CO—O—)

Pro}-DPhg-DTrp-Lys-Tyr(4-Bzl)-Phe], in free form, salt form or protected form. Phg means —HN—CH($C_6H_5$)—CO— and Bzl means benzyl.

A compound of the invention in protected form corresponds to a somatostatin analogue wherein at least one of the amino groups is protected and which by deprotection leads to a compound of formula II or III, preferably physiologically removable. Suitable amino protecting groups are e.g. as disclosed in "Protective Groups in Organic Synthesis", T. W. Greene, J. Wiley & Sons NY (1981), 219-287, the contents of which being incorporated herein by reference. Example of such an amino protecting group is acetyl.

A compound of the invention, e.g. a compound of formula III, for instance Compound A, may exist e.g. in free or salt form. Salts include acid addition salts with e.g. inorganic acids, polymeric acids or organic acids, for example with hydrochloric acid, acetic acid, lactic acid, aspartic acid, benzoic acid, succinic acid or pamoic acid. Acid addition salts may exist as mono- or divalent salts, e.g. depending whether 1 or 2 acid equivalents are added. Preferred salts, e.g. for Compound A, are the lactate, aspartate, benzoate, succinate and pamoate including mono- and di-salts, more preferably the aspartate di-salt and the pamoate monosalt.

The compounds of the invention may be prepared in accordance with conventional methods.

Typically, the compounds of the invention, are delivered systemically, e.g. parenterally. However, parenteral administration may be very painful, especially in repeated administration. In order to minimize the number of injections to a patient, a suitable depot formulation should be administered.

It has been found that administration of microparticles comprising a somatostatin analogue e.g. embedded in a biocompatible pharmacologically acceptable polymer, suspended in a suitable vehicle gives release of all or of substantially all of the active agent over an extended period of time, e.g. several weeks up to 6 months, preferably over at least 4 weeks.

Accordingly, the present invention provides microparticles comprising a compound of, the invention e.g. embedded in a biocompatible pharmacologically acceptable polymer, and a pharmaceutical depot formulation comprising said microparticles.

The compound of the invention may be present in an amount of from about 1 to about 60%, more usually about 10 to about 50%, preferably about 20 to about 40%, even more preferably about 25% to about 35%, by weight of the microparticles dry weight.

Preferably, the compound of the invention used to prepare the microparticles is an amorphous powder having a particle of a size of about 0.1 microns to about 15 microns, preferably less than about 5 microns, even more preferably less than about 3 microns.

The particle size distribution of the compound of the invention may influence the release profile of the drug from the microparticles. Typically, the smaller the particle size, the lower is the burst and release during the first diffusion phase, e.g. the first 20 days. Preferably, particle size distribution is e.g. ×10<0.8 microns i.e. 10% of the particles are smaller than 0.8 microns; ×50<1.5 microns i.e. 50% of the particles are smaller than 1.5 microns; or ×90<3M microns, i.e. 90% of the particles are smaller than 3.0 microns.

The polymer matrix of the microparticles may be a synthetic or natural polymer. The polymer may be either a biodegradable or non-biodegradable or a combination of biodegradable and non-biodegradable polymers, preferably biodegradable.

By "polymer" is meant an homopolymer or a copolymer.

The polymer matrix is designed to degrade sufficiently to be transported from the site of administration within one to 6 months after release of all or substantially all the active agent.

Suitable polymers include (d) linear or branched polyesters which are linear chains radiating from a polyol moiety, e.g. glucose, for example a polyester such as D-, L- or racemic polylactic acid, polyglycolic acid, polyhydroxybutyric acid, polycaprolactone, polyalkylene oxalate, polyalkylene glycol esters of an acid of the Kreb's cycle, e.g. citric acid cycle, and the like or a combination thereof, (e) polymers or copolymers of organic ethers, anhydrides, amides and orthoesters, including such copolymers with other monomers, e.g. a polyanhydride such as a copolymer of 1,3-bis-(p-carboxyphenoxy)-propane and a diacid, e.g. sebacic acid, or a copolymer of erucic acid dimer with sebacic acid; a polyorthoester resulting from reaction of an ortho-ester with a triol, e.g. 1,2,6-hexanetriol, or of a diketene acetal, e.g. 3,9-diethylidene-2,4,8,10-tetraoxaspiro[5,5]un-decane, with a diol, e.g. 1,6-dihexanediol, triethyleneglycol or 1,10-decanediol; or a polyester amide obtained with an amide-diol monomer, e.g. 1,2-di-(hydroxyacetamido)-ethane or 1,10-di-(hydroxyacetamido) decane; or (f) polyvinylalcohol.

The polymers may be cross-linked or non-cross-linked, usually not more than 5%, typically less than 1%.

The preferred polymers of this invention are linear polyesters and branched chain polyesters. The linear polyesters may be prepared from α-hydroxy carboxylic acids, e.g. lactic acid and/or glycolic acid, by condensation of the lactone dimers, see e.g. U.S. Pat. No. 3,773,919, the contents of which are incorporated herein by reference. The preferred polyester chains in the linear or branched (star) polymers are copolymers of the α-carboxylic acid moieties, lactic acid and glycolic acid, or of the lactone dimers. The molar ratio of lactide:glycolide of polylactide-co-glycolides in the linear or branched polyesters is preferably from about 75:25 to 25:75, e.g. 60:40 to 40:60, with from 55:45 to 45:55, e.g. 52:48 to 48:52 the most preferred.

Linear polyesters, e.g. linear polylactide-co-glycolides (PLG), preferably used according to the invention have a weight average molecular weight (Mw) between about 10,000 and about 500,000 Da, e.g. about 50,000 Da. Such polymers have a polydispersity $M_w/M_n$ e.g. between 1.2 and 2. Suitable examples include e.g. poly(D,L-lactide-co-glycolide), e.g. having a general formula —[($C_6H_8O_4$)$_x$($C_4H_4O_4$)$_y$]$_n$— (each of x, y and n having a value so that the total sum gives the above indicated Mws), e.g. those commercially available, e.g. Resomers® from Boehringer Ingelheim, in particular Resomers® RG, e.g. Resomer® RG 502, 502H, 503, 503H, 504, 504H.

Branched polyesters, e.g. branched polylactide-co-glycolides, preferably used according to the invention may be prepared using polyhydroxy compounds e.g. polyol e.g. glucose or mannitol as the initiator. These esters of a polyol are known and described e.g. in GB 2,145,422 B, the contents of which are incorporated herein by reference. The polyol contains at least 3 hydroxy groups and has a molecular weight of up to 20,000 Da, with at least 1, preferably at least 2, e.g. as a mean 3 of the hydroxy groups of the polyol being in the form of ester groups, which contain poly-lactide or co-poly-lactide chains. Typically 0.2% glucose is used to initiate polymerization. The branched polyesters (Glu-PLG) have a central glucose moiety having rays of linear polylactide chains, e.g. they have a star shaped structure.

The branched polyesters having a central glucose moiety having rays of linear polylactide-co-glycolide chains (Glu-PLG) may be prepared by reacting a polyol with a lactide and preferably also a glycolide at an elevated temperature in the presence of a catalyst, which makes a ring opening polymerization feasible.

The branched polyesters having a central glucose moiety having rays of linear polylactide-co-glycolide chains (Glu-PLG) preferably have an weight average molecular weight $M_w$ in the range of from about 10,000 to 200,000, preferably 25,000 to 100,000, especially 35,000 to 60,000, e.g. about 50,000 Da, and a polydispersity e.g. of from 1.7 to 3.0, e.g. 2.0 to 2.5. The intrinsic viscosities of star polymers of $M_w$ 35,000 or $M_w$ 60,000 are 0.36 or 0.51 dl/g, respectively, in chloroform. A star polymer having a $M_w$ 52,000 has a viscosity of 0.475 dl/g in chloroform.

The desired rate of degradation of polymers and the desired release profile for compounds of the invention may be varied depending on the kind of monomer, whether a homo- or a copolymer or whether a mixture of polymers is employed.

A mixture of polymers may comprise at least two different kinds of polymers, e.g. as listed under (a) to (e) above, or two polymers of the same polymer class with different properties. For example, a mixture of polymers may comprise a polymer having a medium weight average molecular weight, e.g. from about 30,000 to about 60,000 Da, e.g. of about 50,000 Da, and of a polymer having a low weight average molecular weight, e.g. of about 2.000 to about 20,000 Da, e.g. of about 10,000 Da.

Preferably, the polymer matrix comprises a linear and/or branched polylactide-co-glycolide. More preferably, the polymer matrix comprises a Resomer® RG, a star polylactide-co-glycolide polymer having a weight average molecular weight of about 10,000 Da and/or a star polylactide-co-glycolide polymer having a weight average molecular weight of about 50,000 Da. The ratio of linear to branched polylactide-co-glycolide preferably is 0:100 to 100:0, e.g. 50:50 to 25:75.

The polymer matrix may be present in a total amount of about 40 to 99% by weight of the microparticles.

The microparticles may further comprise an agent that may influence the porosity of the microparticles. Such an agent may be e.g.

a) Polyvinyl pyrrolidone, preferably with a molecular weight of between about 2,000 and about 20,000 Da. Suitable examples include those commonly known as Povidone K12 F with an average molecular weight of about 2,500 Da, Povidone K15 with an average molecular weight of about 8,000 Da, or Povidone K17 with an average molecular weight of about 10,000 Da.

Preferably, the polyvinyl pyrrolidone is present in an amount of from about 0.1 to about 50%, e.g. about 10%, by weight of the microparticles.

b) Carboxymethyl cellulose sodium (CMC-Na), preferably having a low molecular weight. The viscosity may be, e.g. up to 20 cP for a 2% aqueous solution or a viscosity of from 8 to 25 mPa s. Conveniently the degree of substitution is from about 0.5 to about 1.45, preferably about 0.7. Typically the sodium content is about 5% to about 12%.

Preferably, the CMC-Na is present in an amount of from about 0.1 to about 20%, e.g. about 5%, by weight of the microparticles.

c) Dextrin, e.g. with an average molecular weight ranging from 1,000 to 50,000 Da, preferably 5,000 Da. Preferably the dextrin has a fine particle size distribution, e.g. ×90 less than 20 microns.

Preferably, the dextrin is present in an amount of from about 0.1 to about 10%, e.g. about 5%, by weight of the microparticles.

d) Polyethyleneglycol, e.g. with weight average molecular weight ranging from about 1,000 to about 10,000 Da, preferably from about 1,000 to about 3,350 Da. Suitable examples include those commonly known and commercially available under the trade name Carbowax® from Dow&Union Carbide, with e.g. Mw of 3,350 Da. Polyethyleneglycol with an weight average molecular weight of 3,350 Da has a viscosity of 76 to 110 cSt at 98.9+/−0.3° C. Polyethyleneglycol with Mw ranging from 1000 to 3500 DA has viscosities ranging from 16 to 123 cSt 98.9+/−0.3° C.

The microparticles may further comprise a surfactant. Suitable surfactants include non-ionic surfactants such as a) Poloxamers, also known as polyoxyethylene polyoxypropylene block copolymers, e.g. having a molecular weight from about 2000 to about 8000 Da. The degree of polymerization of the ethylene moiety is typically 80 to about 110 units. The degree of polymerization of the propylene moiety is typically 20 to about 60 units. Examples of such compounds suitable for use in accordance with the present invention are those known and commercially available, e.g. under the trade name Pluronic® F68 available from BASF Germany.

b) Polyoxyethylene-sorbitan-fatty acid esters e.g. mono- and tri-lauryl, palmityl, stearyl and oleyl esters e.g. of the type known and commercially available under the trade name TWEEN®, e.g. Tween 20 [polyoxyethylene(20) sorbitanmonolaurate], Tween 40 [polyoxyethylene(20)sorbitanmonopalmitate], Tween 60 [polyoxyethylene(20)sorbitanmonostearate], Tween 80 [polyoxyethylene(20) sorbitanmonooleate], Tween 65 [polyoxyethylene(20)sorbitantristearate], Tween 85 [polyoxyethylene(20)sorbitantrioleate], Tween 21 [polyoxyethylene(4) sorbitanmonolaurate], Tween 61 [polyoxyethylene(4) sorbitanmonostearate], and Tween 81 [polyoxyethylene(5) sorbitanmonooleate]. Preferred are Tween 20 and Tween 80.

c) Sorbitan fatty acid esters e.g. of the type known and commercially available under the trade name SPAN, for example including sorbitan monolauryl, monopalmityl, monostearyl, tristearyl, monooleyl and trioleyl esters.

d) Lecithins, e.g. soy bean phospholipid, e.g. as known and commercially available under the trade name Lipoid® S75 from Lipoid; or egg phospholipid, e.g. as known and commercially available under the trade names Phospholipon® 90 from Nattermann, Epikuron 100H or Epikuron 145V, Epikuron 170 or Epikuron 200 from Degussa, Bioactives. Preferably, poloxamers, Tween 20 and/or Tween 80 are used.

In case the polymer or polymers used to embed the compound of the invention is a polyester, the microparticles preferably further comprise a basic compound such as a basic salt or a base, e.g. basic zinc carbonate, magnesium hydroxide, magnesium carbonate or a protamine, e.g. human protamine or salmon protamine, or a natural or synthetic polymer bearing amine-residues such as polylysine or dimethylaminoethylmethacrylate.

Reference is made to the extensive literature on the subject for these and other excipients and procedures mentioned herein, see in particular Handbook of Pharmaceutical Excipients, Second Edition, edited by Ainley Wade and Paul J. Weller, American Pharmaceutical Association, Washington, USA and Pharmaceutical Press, London; and Lexikon der Hilfsstoffe für Pharmazie, Kosmetik and angrenzende Gebiete edited by H. P. Fiedler, 4th Edition, Editio Cantor, Aulendorf and earlier editions which are incorporated herein by reference.

Preferably, the microparticles of the invention contain as active ingredient only a compound of the invention, e.g. a compound of formula II, preferably a compound of formula III, even more preferably Compound A. Preferably, the microparticles of the invention contain a compound of the invention, e.g. a compound of formula II or III, in form of the pamoate salt, even more preferably the pamoate salt of Compound A.

Procedures which may be used to prepare the microparticles of the invention may be conventional or known in the art or based on such procedures e.g. those described in L. Lachman et al. The Theory and Practice of Industrial Pharmacy, 3rd Ed, 1986, H. Sucker et al, Pharmazeutische Technologie, Thieme, 1991, Hager's Handbuch der pharmazeutischen Praxis, 4th Ed. (Springer Verlag, 1971), Remington's Pharmaceutical Sciences, 13th Ed., (Mack Publ., Co., 1970) or later editions and in E. Mathiowitz's Encyclopedia of Controlled Drug Delivery (John Wiley & Sons, Inc, 1999).

The present invention in another aspect provides a process for the preparation of microparticles of the invention comprising (i) preparation of an internal organic phase comprising
  (ia) dissolving the polymer or polymers in a suitable organic solvent or solvent mixture,
    and optionally
      dissolving/dispersing a porosity-influencing agent in the solution obtained in step (ia), or
      adding a basic salt to the solution obtained in step (ia),
      adding a surfactant to the solution obtained by step (ia);
  (ib) suspending the compound of the invention in the polymer solution obtained in step (ia), or
    dissolving the compound of the invention in a solvent miscible with the solvent used in step (ia) and mixing said solution with the polymer solution, or
    directly dissolving the compound of the invention in the polymer solution, or
    dissolving the compound of the invention in form of a water soluble salt in an aqueous phase and emulsifying said aqueous solution with the polymer solution (ia);
(ii) preparation of an external aqueous phase comprising
  (iia) preparing a buffer to adjust the pH to 7-7.5, e.g. acetate or phosphate buffer, e.g. $Na_2HPO_4$ and $KH_2PO_4$, and
  (iib) dissolving a stabilizer in the solution obtained in step (iia);
(iii) mixing the internal organic phase with the external aqueous phase e.g. with a device creating high shear forces, e.g. with a turbine or static mixer, to form an emulsion; and
(iv) hardening the microparticles by solvent evaporation or solvent extraction, washing the microparticles, e.g. with water, collecting and drying the microparticles, e.g. freeze-drying or drying under vacuum.

Suitable organic solvents for the polymers include e.g. ethyl acetate, acetone, THF, acetonitrile, or halogenated hydrocarbons, e.g. methylene chloride, chloroform or hexafluoroisopropanol.

Suitable examples of a stabilizer for step (iib) include a) Polyvinyl alcohol (PVA), preferably having a weight average molecular weight from about 10,000 to about 150,000 Da, e.g. about 30,000 Da. Conveniently the polyvinyl alcohol has low viscosity having a dynamic viscosity of from about 3 to about 9 mPa s when measured as a 4% aqueous solution at 20oC or by DIN 53015. Suitably the polyvinyl alcohol may be obtained from hydrolyzing polyvinyl acetate. Preferably, the content of the polyvinyl acetate is from about 10 to about 90% of the polyvinyl alcohol. Conveniently the degree of hydrolysis is about 85 to about 89%. Typically the residual acetyl content is about 10 to 12%. Preferred brands include Mowiol® 4-88, 8-88 and 18-88 available from Clariant AG Switzerland.

Preferably the polyvinyl alcohol is present in an amount of from about 0.1 to about 5%, e.g. about 0.5%, by weight of the volume of the external aqueous phase;

b) Hydroxyethyl cellulose (HEC) and/or hydroxypropyl cellulose (HPC), e.g. formed by reaction of cellulose with ethylene oxide and propylene oxide respectively. HEC and HPC are available in a wide range of viscosity types; preferably the viscosity is medium. Preferred brands include Natrosol® from Hercules Inc., e.g. Natrosol® 250MR, and Klucel® from Hercules Inc.

Preferably, HEC and/or HPC is present in a total amount of from about 0.01 to about 5%, e.g. about 0.5%, by weight of the volume of the external aqueous phase;

c) Polyvinylpyrolidone, e.g. suitably with a molecular weight of between about 2,000 and 20,000 Da. Suitable examples include those commonly known as Povidone K12 F with an average molecular weight of about 2,500 Da, Povidone K15 with an average molecular weight of about 8,000 Da, or Povidone K17 with an average molecular weight of about 10,000 Da. Preferably, the polyvinylpyrolidone is present in an amount of from about 0.1 to about 50%, e.g. 10% by weight of the volume of the external aqueous phase;

d) Gelatin, preferably porcine or fish gelatin. Conveniently, the gelatin has a viscosity of about 25 to about 35 cps for a 10% solution at 20° C. Typically pH of a 10% solution is from about 6 to about 7. A suitable brand has a high molecular weight, e.g. Norland high molecular weight fish gelatin obtainable from Norland Products Inc, Cranbury N.J. USA.

Preferably, the gelatin is present in an amount of from about 0.01 to about 5%, e.g. about 0.5%, by weight of the volume of the external aqueous phase.

Preferably, polyvinyl alcohol is used. Preferably, no gelatin is used. Preferably, the microparticles are gelatin-free.

The resulting microparticles may have a diameter from a few submicrons to a few millimeters; e.g. diameters of at most about 250 microns, e.g. 10 to 200 microns, preferably 10 to 130 microns, more preferably 10 to 90 microns, even more preferably 10 to 60 microns, are strived for, e.g. in order to facilitate passage through an injection needle. A narrow particle size distribution is preferred. For example the particle size distribution may be e.g. x10<15 microns, x50<40 microns or x90<70 microns.

Content uniformity of the microparticles and of a unit dose is excellent. Unit doses may be produced which vary from about 75% to about 125%, e.g. about 85 to about 115%, e.g. from about 90 to about 110%, or from about 95 to about 105%, of the theoretical dose.

The microparticles in dry state may e.g. be mixed, e.g. coated, with an anti-agglomerating agent, or e.g. covered by a layer of an anti-agglomerating agent e.g. in a prefilled syringe or vial.

Suitable anti-agglomerating agents include e.g. mannitol, glucose, dextrose, sucrose, sodium chloride, or water soluble polymers such as polyvinylpyrrolidone or polyethylene glycol, e.g. with the properties described above.

Preferably, an anti-agglomerating agent is present in an amount of about 0.1 to about 10%, e.g. about 4% by weight of the microparticles.

Prior to administration, the microparticles are suspended in a vehicle suitable for injection.

Accordingly, the present invention further provides a pharmaceutical composition comprising microparticles of the invention in a vehicle. The vehicle may optionally further contain: a) one or more wetting agents; and/or b) one or more tonicity agent; and/or c) one or more viscosity increasing agents.

Preferably, the vehicle is water based, e.g. it may contain water, e.g deionized, and optionally a buffer to adjust the pH to 7-7.5, e.g. a phosphate buffer such as a mixture of $Na_2HPO_4$ and $KH_2PO_4$, and one or more of agents a), b) and/or c) as indicated above.

However, when using water as a vehicle, the microparticles of the invention may not suspend and may float on the top of the aqueous phase. In order to improve the capacity of the microparticles of the invention to be suspended in an aqueous medium, the vehicle preferably comprises a wetting agent a). The wetting agent is chosen to allow a quick and suitable suspendibility of the microparticles in the vehicle. Preferably, the microparticles are quickly wettened by the vehicle and quickly form a suspension therein.

Suitable wetting agents for suspending the microparticles of the invention in a water-based vehicle include non-ionic surfactants such as poloxamers, or polyoxyethylene-sorbitan-fatty acid esters, the characteristics of which have been described above. A mixture of wetting agents may be used. Preferably, the wetting agent comprises Pluronic F68, Tween 20 and/or Tween 80.

The wetting agent or agents may be present in about 0.01 to about 1% by weight of the composition to be administered, preferably from 0.01 to 0.5% and may be present in about 0.01 to 5 mg/ml of the vehicle, e.g. about 2 mg/ml.

Preferably, the vehicle further comprises a tonicity agent b) such as mannitol, sodium chloride, glucose, dextrose, sucrose, or glycerin. Preferably, the tonicity agent is mannitol.

The amount of tonicity agent is chosen to adjust the isotonicity of the composition to be administered. In case a tonicity agent is contained in the microparticles, e.g. to reduce agglomeration as mentioned above, the amount of tonicity agent is to be understood as the sum of both. For example, mannitol preferably may be from about 1% to about 5% by weight of the composition to be administered, preferably about 4.5%.

Preferably, the vehicle further comprises a viscosity increasing agent c). Suitable viscosity increasing agents include carboxymethyl cellulose sodium (CMC-Na), sorbitol, polyvinylpyrrolidone, or aluminium monostearate.

CMC-Na with a low viscosity may conveniently be used. Embodiments may be as described above. Typically, a CMC-Na with a low molecular weight is used. The viscosity may be of from about 1 to about 30 mPa s, e.g. from about 10 to about 15 mPa s when measured as a 1% (w/v) aqueous solution at 25° C. in a Brookfield LVT viscometer with a spindle 1 at 60 rpm, or a viscosity of 1 to 15 mPa*s for a solution of NaCMC 7LF (low molecular weight) as a 0.1 to 1% solution in water.

A polyvinylpyrrolidone having properties as described above may be used.

A viscosity increasing agent, e.g. CMC-Na, may be present in an amount of from about 0.1 to about 2%, e.g. about 0.7% or about 1.75% of the vehicle (by volume), e.g. in a concentration of about 1 to about 30 mg/ml in the vehicle, e.g. about 7 mg/ml or about 17.5 mg/ml.

In a further aspect, the present invention provides a kit comprising microparticles of the invention and a vehicle of the invention. For example, the kit may comprise microparticles comprising the exact amount of compound of the invention to be administered, e.g. as described below, and about 1 to about 5 ml, e.g. about 2 ml of the vehicle of the invention.

In one embodiment, the dry microparticles, optionally in admixture with an anti-agglomerating agent, may be filled into a container, e.g. a vial or a syringe, and sterilized e.g. using γ-irradition. Prior to administration, the microparticles may be suspended in the container by adding a suitable vehicle, e.g. the vehicle described above. For example, the microparticles, optionally in admixture with an anti-agglomerating agent, a viscosity increasing agent and/or a tonicity agent, and the vehicle for suspension may be housed separately in a double chamber syringe. A mixture of the microparticles with an anti-agglomerating agent and/or a viscosity increasing agent and/or a tonicity agent, also forms part of the invention.

In another embodiment, under sterile conditions dry sterilized microparticles, optionally in admixture with an anti-agglomerating agent, may be suspended in a suitable vehicle, e.g. the vehicle described above, and filled into a container, e.g. a vial or a syringe. The solvent of the vehicle, e.g. the water, may then be removed, e.g. by freeze-drying or evaporation under vacuum, leading to a mixture of the microparticles and the solid components of the vehicle in the container. Prior to administration, the microparticles and solid components of the vehicle may be suspended in the container by adding a suitable vehicle, e.g. water, e.g. water for infusion, or preferably a low molarity phosphate buffer solution. For example, the mixture of the microparticles, optionally the anti-agglomerating agent, and solid components of the vehicle and the vehicle for suspension, e.g. water, may be housed separately in a double chamber syringe.

The microparticles and the compositions of the invention are useful f) for the prevention or treatment of disorders with an aetiology comprising or associated with excess GH-secretion and/or excess of IGF-1 e.g. in the treatment of acromegaly as well as in the treatment of type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity, g) in the treatment of enterocutaneous and pancreaticocutaneous fistula, irritable bowel syndrom, inflammatory diseases, e.g. Grave's Disease, inflammatory bowel disease, psoriasis or rheumatoid arthritis, polycystic kidney disease, dumping syndrom, watery diarrhea syndrom, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding, h) for the prevention or treatment of angiogenesis, inflammatory disorders as indicated above including inflammatory eye diseases, macular edema, e.g. cystoid macular edema, idiopathic cystoid macular edema, exudative age-related macular degeneration, choroidal neovascularization related disorders and proliferative retinopathy, i) for preventing or combating graft vessel diseases, e.g. alto- or xenotransplant vasculopathies, e.g. graft vessel atherosclerosis, e.g. in a transplant of organ, e.g. heart, lung, combined heart-lung, liver, kidney or pancreatic transplants, or for preventing or treating vein graft stenosis, restenosis and/or vascular occlusion following vascular injury, e.g. caused by catherization procedures or vascular scraping procedures such as percutaneous transluminal angioplasty, laser treatment or other invasive procedures which disrupt the integrity of the vascular intima or endothelium, j) for treating somatostatin receptor expressing or accumulating tumors such as pituitary tumors, e.g. Cushing's Disease or Syndrome, gastro-enteropancreatic, carcinoids, central nervous system, breast, prostatic (including advanced hormone-refractory prostate cancer), ovarian or colonic tumors, small cell lung cancer, malignant bowel obstruction, paragangliomas, kidney cancer, skin cancer, neuroblastomas, pheochromocytomas, medullary thyroid carcinomas, myelomas, lymphomas, Hodgkins and non-Hodgkins lymphomas, bone tumours and metastases thereof, as well as autoimmune or inflammatory disorders, e.g. rheumatoid arthritis, Graves disease or other inflammatory eye diseases.

Preferably, the microparticles and the compositions of the invention are useful in the treatment of acromegaly and cancer, e.g. Cushing's Disease or Syndrome, carcinoids.

The properties of the microparticles and the compositions of the invention may be tested in standard animal tests or clinical trials.

The microparticles and the compositions of the invention are well-tolerated.

The compounds of the invention are released from the microparticles of the invention and from the compositions of the invention over a period of several weeks e.g. about 4 weeks to 6 months.

Appropriate dosage of the composition of the invention will of course vary, e.g. depending on the condition to be treated (for example the disease type or the nature of resistance), the drug used, the effect desired and the mode of administration.

In general, satisfactory results are obtained on administration, e.g. parenteral administration, at dosages on the order of from about 0.2 to about 100 mg, e.g. 0.2 to about 35 mg, preferably from about 3 to about 100 mg of the compound of the invention per injection per month or about 0.03 to about 1.2 mg, e.g. 0.03 to 0.3 mg per kg animal body weight per month. Suitable monthly dosages for patients are thus in the order of about 0.3 mg to about 100 mg of a compound of the invention, e.g. a compound of formula III, e.g. Compound A.

The following Examples serve to illustrate the invention, without any limitation

EXAMPLES 1 TO 4

Microparticles

The poly-(D,L-lactide-co-glycolide) is dissolved in an amount of methylene chloride as indicated in Table 1. The polymer solution is then added to the Compound A pamoate. The resulting suspension is treated with an Ultra-Turrax for 1 min.

2 l of water are heated to 90° C. During warming, the phosphate salts in an amount as given in Table 1 are added one after another. At 90° C., PVA 18-88 in an amount as given in Table 1 is added. The resulting solution is then cooled to 20° C. and filled up with water to the required volume.

The polymer/drug suspension and the PVA/phosphate solution are mixed, methylene chloride is evaporated under vacuum and the microparticles are filtered off, washed with water (WBU) and dried under reduced pressure (0.1 mbar) at room temperature.

TABLE 1

| (Amounts given in g) | | | | | |
|---|---|---|---|---|---|
| | Ex. 1 | Ex. 2a | Ex. 2b | Ex. 3 | Ex. 4 |
| Star polymer: Poly-(D,L-lactide-co-glycolide) with a $M_w$ of about 50,000 Da Molar Ratio lactide:glycolide 50:50 | 2.266 | 2.555 | 2.555 | 1.977 | 2.555 |
| Methylene chloride | 15.035 | 22.603 | 22.603 | 13.117 | 16.926 |
| Compound A pamoate | 1.734 | 1.445[1] | 1.445[2] | 2.023 | 1.445 |
| Polyvinyl alcohol (PVA) 18-88 | 15.00 | 15.00 | 15.00 | 15.00 | 15.00 |
| K $H_2PO_4$ | 5.43 | 5.43 | 5.43 | 5.43 | 5.43 |
| $Na_2 HPO_4$ anhydrous | 22.71 | 22.71 | 22.71 | 22.71 | 22.71 |
| Water (WBU) | Ad 3.0 l | Ad 3.0 l | Ad 3.0 l | Ad 3.0 l | Ad 3.0 l |

[1]Particle size distribution: x90 < 15 microns
[2]Particle size distribution: x90 < 3 microns

EXAMPLES 5 TO 8

Microparticles

TABLE 2

| (Amounts given in g) | | | | |
|---|---|---|---|---|
| | Ex. 5 | Ex. 6 | Ex. 7 | Ex. 8 |
| Star polymer: Poly-(D,L-lactide-co-glycolide) with a $M_w$ of about 50,000 Da Molar Ratio lactide:glycolide 50:50 | 1.916 | 1.916 | 1.278 | 1.278 |
| Star polymer: Poly-(D,L-lactide-co-glycolide) with a $M_w$ of about 16,500 Da Molar Ratio lactide:glycolide 50:50 | 0.639 | — | 1.278 | — |
| Resomer RG 502H Molar Ratio lactide:glycolide 50:50 | — | 0.639 | — | 1.278 |
| Methylene chloride | 16.926 | 16.926 | 16.926 | 16.926 |
| Compound A pamoate | 1.445 | 1.445 | 1.445 | 1.445 |
| Polyvinyl alcohol (PVA) 18-88 | 15.00 | 15.00 | 15.00 | 15.00 |
| K $H_2PO_4$ | 5.43 | 5.43 | 5.43 | 5.43 |
| $Na_2 HPO_4$ anhydrous | 22.71 | 22.71 | 22.71 | 22.71 |
| Water (WBU) | Ad 3.0 l | Ad 3.0 l | Ad 3.0 l | Ad 3.0 l |

The polymers are dissolved in an amount of methylene chloride as indicated in Table 2. The polymer solution is then added to the Compound A pamoate. The resulting suspension is treated with an Ultra-Turrax for 1 min.

2 l of water are heated to 90° C. During warming, the phosphate salts in an amount as given in Table 2 are added one after another. At 90° C., PVA 18-88 in an amount as given in Table 2 is added. The resulting solution is then cooled to 20° C. and filled up with water to the required volume.

The polymer/drug suspension and the PVA/phosphate solution are mixed, methylene chloride is evaporated under vacuum, and the microparticles are filtered off, washed with water (WBU) and dried under reduced pressure (0.1 mbar) at room temperature.

EXAMPLE 10

Vehicle Compositions A to G

CMC-Na, Mannitol and Pluronic F68 in an amount as given in Table 3 are dissolved in about 15 ml hot deionized water of a temperature of about 90° C. under strong stirring with a magnetic stirrer. The resulting clear solution is cooled to 20° C. and filled up with deionized water to 20.0 ml.

TABLE 3

(Amounts given in g)

| | A | B | C | D | E | F | G |
|---|---|---|---|---|---|---|---|
| CMC-Na | 0 | 0 | 0.05 | 0.14 | 0.28 | 0.35 | 0.40 |
| Mannitol | 0 | 1.04 | 0.99 | 0.90 | 0.76 | 0.74 | 0.68 |
| Pluronic F68 | 0.04 | 0.04 | 0.04 | 0.04 | 0.04 | 0.04 | 0.04 |

Vehicle E is preferred for use in double chamber syringe.

EXAMPLE 10

384 mg or 576 mg of microparticles of example 2a and 2b are suspended in 2.0 ml of a vehicle of composition D in 6R vials. The suspensions are homogenized by shaking for about 30 seconds. The reconstituted suspension may be injected without any issues using a 20 Gauge needle.

EXAMPLE 11

240 mg of microparticles of example 2a and 2b are reconstituted in 1 ml of the vehicle composition F, homogenized with a propeller mixer at 400 rpm for 1 to 12 hours and then freeze-dried in a Telstar lyophilisator.

Reconstitution of the microparticle lyophilisates with 1 ml pure water (WBU) resulted in fast and good wetting of the microparticles that may be injected without any issues using a 20 Gauge needle.

EXAMPLE 12

Release of Compound A from Microparticles

Microparticles of example 2a and 2b in an amount corresponding to 4 mg of Compound A per kg of the rabbit are suspended in 1 ml of the vehicle composition D. The suspension is homogenized by shaking for about 30 seconds and injected into the left Musculus gastronemius of rabbits, weighing about 3 kg before onset of the study, using an 18G needle.

Blood samples (about 1 ml) are collected over 55 days. Plasma levels of Compound A are determined using an ELISA method. Mean concentration of Compound A after administration is given in Table 4. Mean AUC(0-55 d) is found to be 454 ng/ml d for example 2a and 296 ng/ml d for example 2b.

TABLE 4

(mean concentration in ng/ml)

| | Time after administration [days] | | | | | | | | | |
|---|---|---|---|---|---|---|---|---|---|---|
| | 0 | 0.021 | 0.042 | 0.083 | 0.167 | 0.25 | 1 | 2 | 3 | 6 | 9 |
| Microparticles of ex. 2a | 0 | 9.10 | 9.72 | 10.18 | 8.67 | 6.29 | 4.61 | 4.67 | 4.75 | 7.45 | 3.46 |
| Microparticles of ex. 2b | 0 | 0 | 0 | 0 | 0 | 0 | 0 | 0 | 0.87 | 1.06 | 0.65 |

| | Time after administration [days] | | | | | | | | | | |
|---|---|---|---|---|---|---|---|---|---|---|---|
| | 13 | 16 | 20 | 23 | 27 | 30 | 34 | 37 | 41 | 44 | 48 | 55 |
| Microparticles of ex. 2a | 2.10 | 1.65 | 4.62 | 8.95 | 16.39 | 18.71 | 26.97 | 12.50 | 7.33 | 5.52 | 4.04 | 2.25 |
| Microparticles of ex. 2b | 0 | 0 | 7.93 | 15.71 | 18.74 | 16.04 | 8.94 | 6.45 | 3.75 | 2.17 | 1.23 | 0.68 |

The invention claimed is:

1. Microparticles comprising cyclo[{4-(NH$_2$—C$_2$H$_4$—NH—CO—O—)Pro}-Phg-DTrp-Lys-Tyr(4-Bzl)-Phe] in free form, salt form or protected form embedded in a polymer matrix wherein the polymer matrix comprises a linear and a star polylactide-co-glycolide.

2. Microparticles according to claim 1 wherein the cyclo[{4-(NH$_2$—C$_2$H$_4$—NH—CO—O—)Pro}-Phg-DTrp-Lys-Tyr(4-Bzl)-Phe] is in pamoate salt form.

3. Microparticles according to claim 1 wherein the polymer matrix comprises a linear polylactide-co-glycolide polymer and a star polylactide-co-glycolide polymer having a weight average molecular weight of about 50,000 Da.

4. Microparticles according to claim 1 wherein the ratio of linear to star polylactide-co-glycolide is 50:50.

5. Microparticles according to claim 1 wherein the cyclo[{4-(NH$_2$—C$_2$H$_4$—NH—CO—O—)Pro}-Phg-DTrp-Lys-Tyr(4-Bzl)-Phe] is an amourphous powder having a particle size less than about 5 microns.

6. Microparticles according to claim 1 further comprising a surfactant, a porosity influencing agent and/or a basic salt.

7. A pharmaceutical composition comprising microparticles according to claim 1 and a water-based vehicle comprising a wetting agent.

8. A composition according to claim 7 wherein the wetting agent comprises a poloxamer and/or a polyoxyethylene-sorbitan-fatty acid ester.

9. A composition according to any one of claim 7 wherein the vehicle comprises a tonicity agent.

10. A composition according to any one of claim 7 wherein the vehicle comprises a viscosity increasing agent.

11. A kit comprising microparticles according to claim 1 and a water-based vehicle.

* * * * *